United States Patent [19]
Schroder

[11] Patent Number: 6,143,030
[45] Date of Patent: Nov. 7, 2000

[54] IMPACTION ALLOGRAFT FORM AND METHOD OF ORTHOPAEDIC SURGERY USING SAME

[75] Inventor: Lisa K. Schroder, Rochester, Ind.

[73] Assignee: Bristol-Myers Squibb Co., New York, N.Y.

[21] Appl. No.: 09/277,594

[22] Filed: Mar. 26, 1999

[51] Int. Cl.[7] .................................................. A61F 2/02
[52] U.S. Cl. .................. 623/16.11; 623/23.63; 623/23.34; 623/919
[58] Field of Search ............... 623/16.11, 23.72, 623/20.35, 20.36, 23.15, 23.34, 17.11, 17.16, 908, 919, 923, 925

[56] References Cited

U.S. PATENT DOCUMENTS

| 5,591,232 | 1/1997 | Rahimi et al. ............... 623/23.72 |
| 5,658,332 | 8/1997 | Ducheyne et al. ............ 623/23.72 |
| 5,700,289 | 12/1997 | Breitbart et al. ............. 623/23.72 |
| 5,899,939 | 5/1999 | Boyce et al. ................ 623/23.72 |
| 5,941,909 | 8/1999 | Purkait ...................... 623/23.34 |
| 6,033,438 | 3/2000 | Bianchi et al. ............... 623/17.16 |

OTHER PUBLICATIONS

The Use of Bone Allografts in the Spine; Glenn R. Buttermann et al.; Clinical Orthopaedics and Related Research No. 324, pp 75–85, 1996.

Unilab Surgibone for Surgical Implant *Journal of Bone and Joint Surgery*, Nov. 1987 vol. 69–B.

*Primary Examiner*—David H. Willse
*Assistant Examiner*—Suzette J. Jackson
*Attorney, Agent, or Firm*—Cary R. Reeves

[57] ABSTRACT

A method of performing orthopaedic surgery on a bone includes the steps of: preparing an allograft form including a plurality of allograft bone particles with a predetermined outside shape (e.g., cylindrical or implant shaped); freezing the allograft form; placing the frozen allograft form in an opening in the bone; and impacting the frozen allograft form within the opening to cause the allograft form to at least partially fill the opening. The form includes a cannulation hole extending therethrough.

22 Claims, 3 Drawing Sheets

6,143,030

1

IMPACTION ALLOGRAFT FORM AND METHOD OF ORTHOPAEDIC SURGERY USING SAME

BACKGROUND OF THE INVENTION

1. Field of the Invention

The present invention relates to orthopaedic implants, and, more particularly, to orthopaedic bodies which are inserted into an opening in a bone during orthopaedic surgery.

2. Description of the Related Art

An orthopaedic implant is typically implanted into an end of a bone, such as the proximal end of a femur. Occasionally, the bone includes an opening which is larger than necessary to receive the orthopaedic implant. For example, an end of a bone which is to receive a revision implant during a revision orthopaedic surgery may include an opening which is larger than the new revision implant which is to be implanted. As another example, a bone may include an opening which is larger than an implant as a result of a disease condition such as cancer. It is occasionally thus necessary to fill an enlarged opening in a bone to a desired extent to form a "neo-medullary" canal of appropriate size and shape to receive an implant.

A known method of filling an opening in a bone is to impact bone chips into the intramedullary (IM) canal to partially fill the IM canal. Such bone chips are commonly obtained from similar bones retrieved from donor cadavers. Such bone chips are known as "allograft" bone chips since they are obtained from cadavers. The bones are normally kept in a frozen state within a hospital and the surgeon grinds up the bones immediately prior to surgery. The bone chips are then poured into the opening in the bone and impacted in the opening using successively smaller tamps until a neo-medullary canal of proper size and shape is formed. A layer of bone cement is injected into the neo-medullary canal and the implant is cemented into the bone.

A problem with using allograft bone chips as described above is that the effectiveness of the technique is in large part dependent upon the skill of the surgeon. The size and shape of the bone particles may vary dependent upon how the bone particles are formed. Additionally, the type of tamp and force used during the tamping affects the impaction of the bone particles within the opening in the bone.

What is needed in the art is a surgical technique which allows a surgeon to more easily use an impaction allograft technique, and which reduces variability associated with presently uncontrolled parameters.

SUMMARY OF THE INVENTION

The present invention provides an impaction allograft form with a plurality of bone particles which are frozen together into a pre-shaped form which may be inserted into an opening in a bone during orthopaedic surgery.

The invention comprises, in one form thereof, a method of performing orthopaedic surgery on a bone, including the steps of: preparing an allograft form with a predetermined outside shape and including a plurality of allograft bone particles; freezing the allograft form; placing the frozen allograft form in an opening in the bone; and impacting the frozen allograft form within the opening to cause the allograft form to at least partially fill the opening.

The invention comprises, in another form thereof, an orthopaedic body for insertion into an opening in a bone during orthopaedic surgery. The orthopaedic body includes an impaction allograft form with a plurality of allograft bone particles frozen together with a predetermined outside shape. The form includes a cannulation hole extending therethrough.

An advantage of the present invention is that the allograft form can be installed into an opening in a bone as a preformed body.

Another advantage is that the quality and consistency of the allograft form can be better controlled.

Yet another advantage is that the time necessary to impact the allograft bone within the bone is reduced.

A further advantage is that the allograft form can be coated or mixed with a bone growth enhancer to stimulate bone growth into the allograft form.

A still further advantage is that different allograft forms can be made with different outside shapes which allow the form to optimally fit the opening in the bone.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
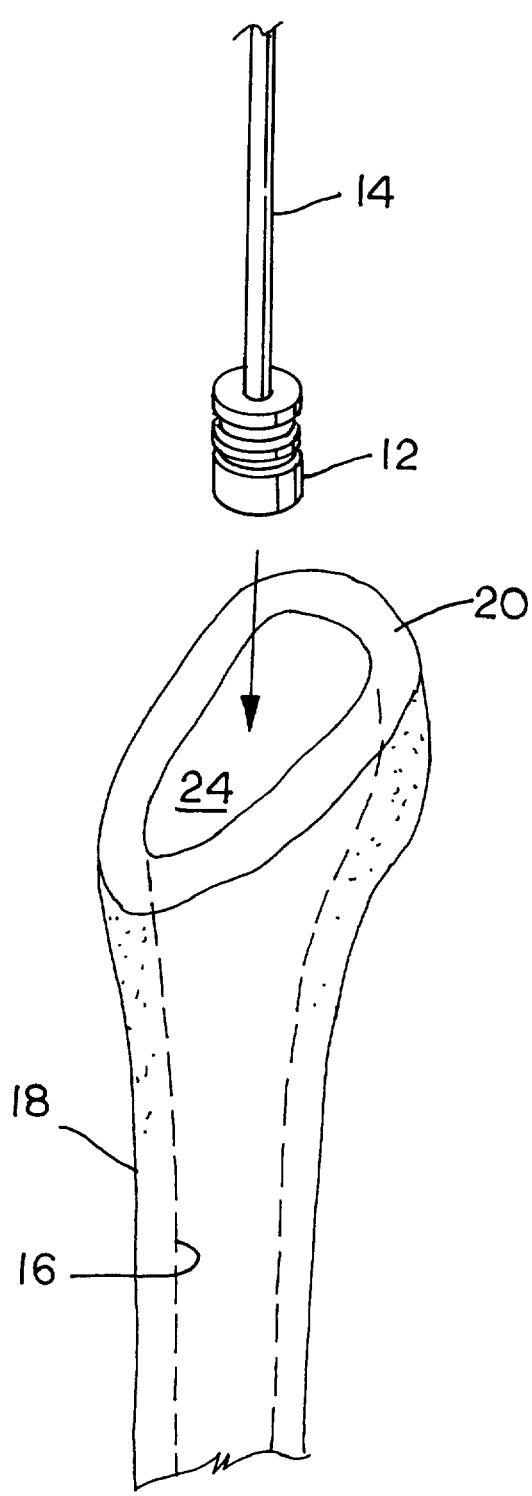
FIG. 1 is a perspective view of a femur having an opening into which a guide wire and plug are inserted.
Figure 2:
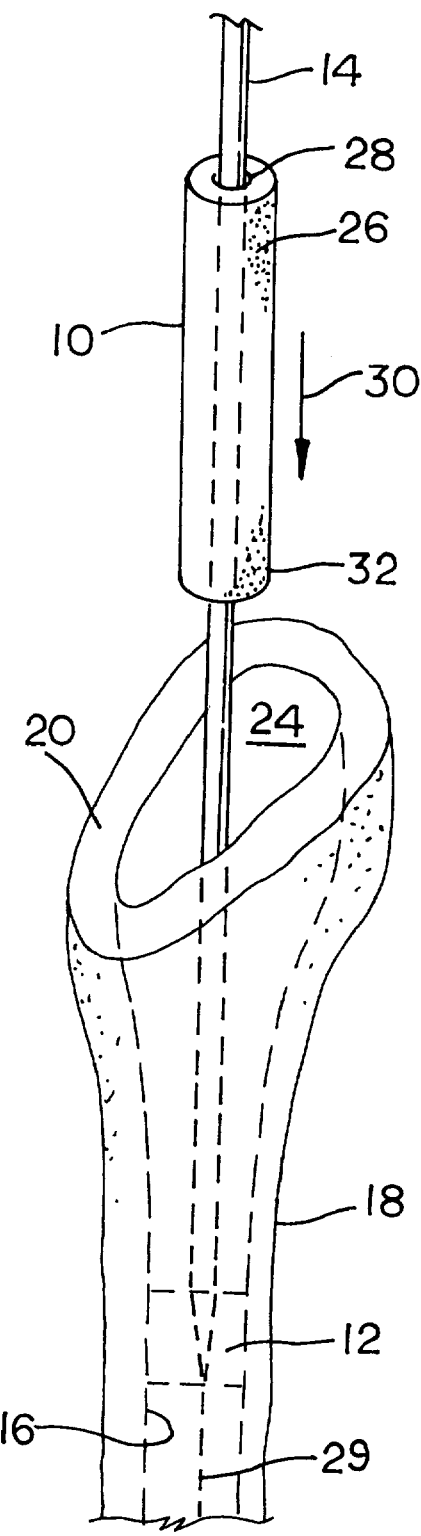
FIG. 2 illustrates an embodiment of an allograft form of the present invention being slid over the guide wire and placed into the opening in the femur.
Figure 3:
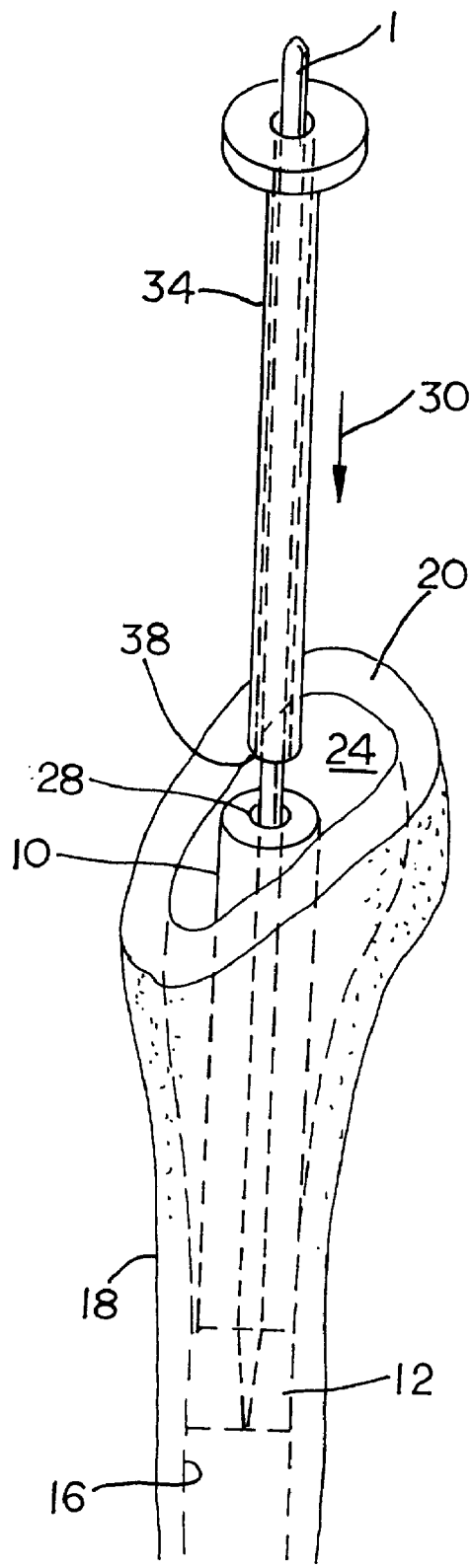
FIG. 3 illustrates impaction of the allograft form using a cylindrical tamp.

Referring now to the drawings, and more particularly to FIGS. 1–5, an embodiment of an impaction allograft form 10 of the present invention and a method of performing orthopaedic surgery using allograft form 10 will be described. Allograft form 10 shown in FIGS. 1–4 is illustrated for use with a femur 18. However, it is to be understood that allograft form 10 and the method of manufacture and surgery using allograft form 10 may be carried out on any bone where use of an impaction allograft technique is necessary or desirable.

During a normal orthopaedic surgery using allograft bone particles to fill in part of an opening in a bone such as femur 18, a plug 12 is attached to a guide wire 14, such as by piercing a sharpened end of guide wire 14 into plug 12. Plug 12 is selected with an outside diameter which closely approximates the inside diameter of an IM canal 16 within femur 18. Guide wire 14 is used to place plug 12 within IM canal 16 in femur 18. Plug 12 is inserted from proximal end 20 of femur 18 to a depth which is beyond the length of a femoral implant 22 (FIG. 5) to be implanted within femur 18. Normally, after plug 12 and guide wire 14 are placed within femur 18, loose bone chips are poured into opening 24 in proximal end 20 of femur 18 and impacted within opening 24 using successively smaller tamps until opening 24 is filled to a desired amount.

When using loose bone chips as described above, the quality and consistency of the bone chips varies depending upon the equipment used to make the bone chips, the skill of the surgeon, the impaction technique utilized, etc. Accordingly, the results of conventional impaction allograft techniques very widely dependent upon the skill of the surgeon and other uncontrolled factors.

According to an aspect of the present invention, loose bone particles are not poured into opening 24 of femur 18. Rather, a preformed impaction allograft form 10 is provided. Allograft form 10 can have any predetermined outside shape and includes a plurality of allograft bone particles, a portion of which are shown and referenced as 26. Rather than being formed during surgery by a surgeon, bone particles 26 are formed in a manufacturing setting under much tighter controls and tolerances. Bone particles 26 may be screened or otherwise sorted so that the particles are of substantially uniform size and shape. In the embodiment shown, bone particles 26 are in the form of bone chips with a controlled size and shape. The size and shape of bone particles 26 may vary from one allograft form 10 to another so that a surgeon may select an allograft form 10 with bone particles 26 which are suitable for a specific application.

Allograft form 10 includes a cannulation hole 28 which extends the longitudinal length thereof, and which has a diameter which is at least slightly larger than the diameter of guide wire 14. Cannulation hole 28 allows allograft form 10 to be slide over guide wire 14, as indicated by directional arrow 30. Since guide wire 14 substantially coincides with an anatomical axis 29 of femur 18, cannulation hole 28 also substantially aligns with anatomical axis 29 when allograft form 10 is slid over guide wire 14.

Allograft form 10 may also include a coating of a bone growth enhancer 32 over the exterior thereof. Bone growth enhancer 32 stimulates live bone in femur 18 to grow into the porous surface of allograft form 10, thereby interlocking the impacted allograft bone particles with femur 18. Bone growth enhancer 32 is in the form of either hydroxylapatite (HA) or hydroxylapatite-tricalciumphosphate (HATCP) in the embodiment shown; however, other bone growth enhancers may be utilized such as bone morphogenic protein (BMP).

As indicated above, allograft form 10 may be configured with any suitable exterior size and shape. In the embodiment shown in FIGS. 1–4, allograft form 10 has a cylindrical outside shape with an outside diameter which is just slightly smaller than the inside diameter of IM canal 16 of femur 18. A plurality of allograft forms 10 may be provided with different diameters so that a surgeon may select an allograft form 10 which fills opening 24 in femur 18 to a desired extent More than one graft form 10 may be used advantageously to fill opening 24 by using forms with different diameters at different locations within opening 24.

During manufacture, bone particles 26 are formed by grinding, machining, etc., selected bones such as femurs. The bone particles may be screened, sorted or graded so that bone particles 26 of a selected size and shape are segregated together. Bone chips 26 are then placed within a mold (not shown) having a shape which is complimentary to the desired shape of an allograft form 10 which is to be manufactured. Bone particles 26 may be loosely placed within the mold, but are preferably compressed within the mold to a desired extent. The mold with the bone chips therein is then frozen and the moisture within the bone chips bonds the bone chips together when in a frozen state. It is also possible to add a liquid such as sterile water to the bone chips within the mold to ensure that the bone chips freeze together. When frozen, allograft form 10 is removed from the mold and placed within a freezer for further use by a surgeon. Alternatively, dependent upon factors such as moisture content, particle size and shape, and/or the presence of a temporary binding additive, it may also be possible to compact bone particles within the mold and remove allograft form 10 from the mold prior to freezing.

During surgery, guide wire 14 is inserted into plug 12. Plug 12 is then inserted into IM canal 16 of femur 18 to a proper depth, as described above and shown in FIG. 2. Allograft form 10 is then slid over guide wire 14 such that cannulation hole 28 surrounds guide wire 14. Allograft form 10 is then slid into opening 24 of femur 18, as indicated by arrow 30 in FIG. 2. When allograft form 10 is placed within IM canal 16 (FIG. 3), a series of progressively larger tamps 34 and 36 are used to both axially and radially impact allograft form 10 within opening 24 to cause allograft form 10 to at least partially fill opening 24 to a desired extent. Tamp 34 has a cylindrical shape with an outside diameter which is larger than the inside diameter of cannulation hole 28 in allograft form 10. Preferably, the outside diameter of cylindrical tamp 34 is selected so that the leading end 38 of cylindrical tamp 34 at least partially slides into cannulation hole 28 to radially expand allograft form 10 as tamp 34 is repeatedly moved in an axial direction 30 against allograft form 10. A series of cylindrical tamps 34 with progressively larger diameters may be utilized if desired.

Figure 4:
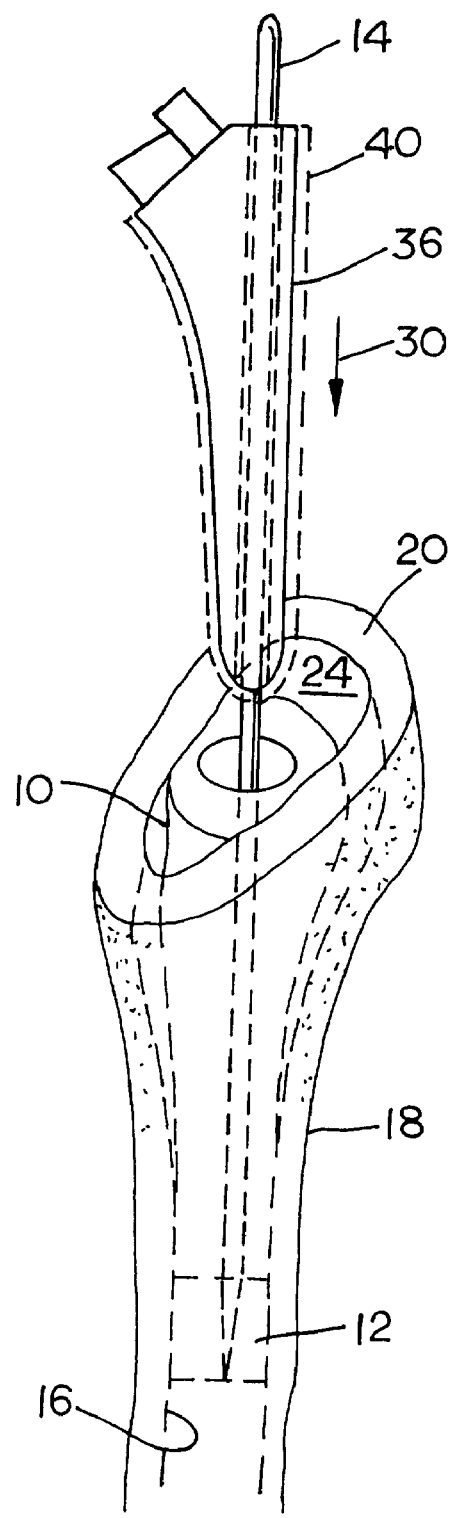
FIG. 4 illustrates further impaction of the allograft form using an implant-shaped tamp.
Figure 5:
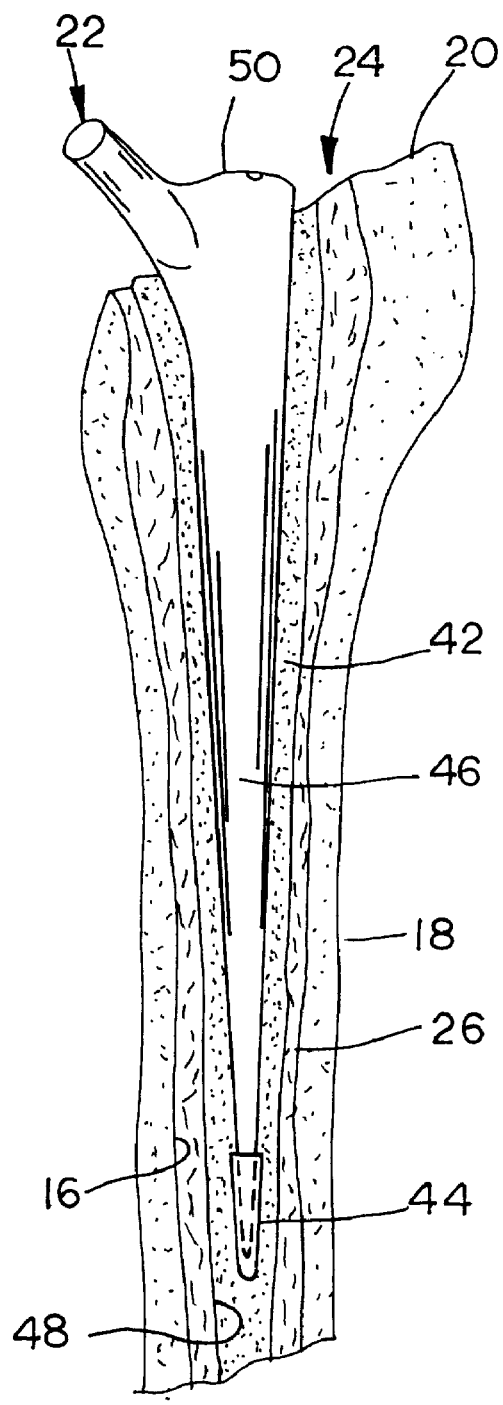
FIG. 5 illustrates an implant in the femur after the allograft form has been impacted.

Tamp 36 illustrated in FIG. 4 has an outside shape which approximates an implant 22 to be implanted within femur 18. Tamp 36 is normally used after one or more cylindrical tamps 34 are used. However, implant-shaped tamp 36 may be used in place of cylindrical tamp 34.

After allograft form 10 has been expanded to some extent as shown in FIG. 4, tamp 36 may be used to further expand allograft form 10 within opening 24 and define a neo-medullary canal for receiving an implant 22 to be implanted within femur 18. A series of tamps 36 with progressively larger outside sizes may be used, as indicated by phantom line 40 in FIG. 4. Additional allograft forms 10 may be inserted over guide wire 14 as necessary. It is also possible to pour in a limited amount of loose bone particles 26 at proximal end 20 during the final impacting stages of bone particles 26 within femur 18.

After bone particles 26 are impacted within IM canal 16 to a desired extent (FIG. 5), bone cement 42 is placed within neo-medullary canal 48. Preferably the bone cement is pressurized such that it is incorporated into, or interdigitates to some extent, with the allograft. A distal centralizer 44 is placed over the distal end of stem 46 of implant 22 to keep the distal end of stem 46 substantially centered within neo-medullary canal 48 such that bone cement 42 substantially surrounds stem 46. Implant 22 may be oriented to obtain a proper alignment relative to an acetabular cup with which it mates, in known manner. Implant 22 is then placed into neo-medullary canal 48 until proximal end 50 extends from opening 24 in femur 18 a desired amount.

Figure 6:
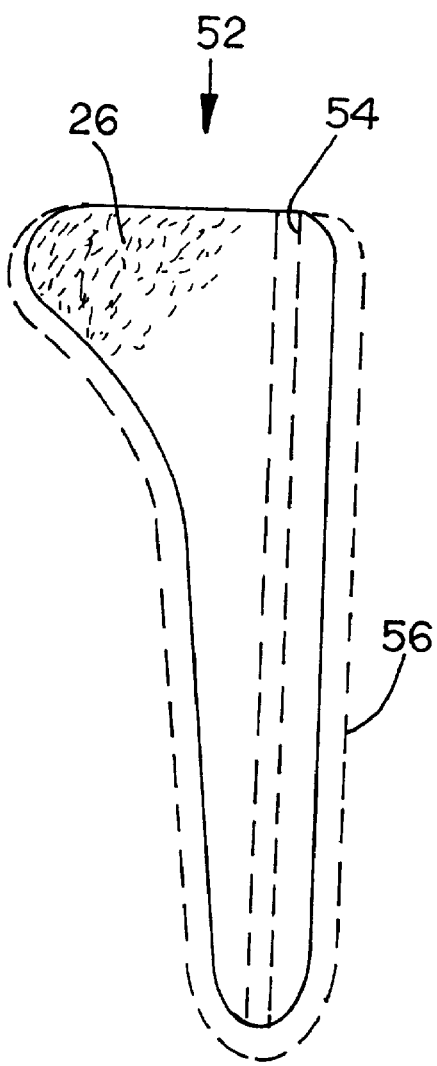
FIG. 6 illustrates another embodiment of an allograft form of the present invention.

FIG. 6 illustrates another embodiment of an impaction allograft form 52 of the present invention. Allograft form 52 has an outside shape which approximates the shape of the IM canal. Such a canal shaped allograft form advantageously has features such as a medial curve, trapezoidal cross-section, and/or a distal-to-proximal anterior/posterior flare so that the form fills the canal as much as possible and matches the known canal geometry as closely as possible. Final fitting is accomplished by tamping as described above. Alternatively, the allograft form 52 has an outside shape which approximates the shape of the implant 22 to be implanted within femur 18. Allograft form 52 includes a plurality of bone particles 26 with a controlled size and shape, similar to bone particles 26 shown in FIGS. 1–5. Allograft form 52 also includes a cannulation hole 54, similar to carmulation hole 28 of allograft form 10. Allograft form 52 may be formed with any suitable size such as the larger size indicated by phantom line 56, so that a surgeon may select an allograft form 52 which better fills opening 24 in femur 18 to a desired extent.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method of performing orthopaedic surgery on a bone, comprising the steps of:
   preparing an allograft form with a predetermined outside shape and including a plurality of allograft bone particles;
   freezing said allograft form;
   placing said frozen allograft form in an opening in the bone; and
   impacting said frozen allograft form within said opening to cause said allograft form to at least partially fill said opening.

2. The method of claim 1, wherein said allograft form has an outside shape which is substantially cylindrical.

3. The method of claim 1, wherein said allograft form has an outside shape which approximates an implant to be implanted within the bone.

4. The method of claim 1, wherein said allograft form includes a cannulation hole.

5. The method of claim 4, wherein said placing step includes the substep of aligning said cannulation hole substantially parallel with an anatomical axis of the bone.

6. The method of claim 4, comprising the further step of positioning a guide wire within said opening in the bone, and wherein said placing step comprises the substep of sliding said cannulation hole over said guide wire.

7. The method of claim 6, wherein said opening in the bone comprises an intramedullary canal, and comprising the further steps of placing a plug within said intramedullary canal, and attaching said guide wire with said plug.

8. The method of claim 1, wherein said impacting step is carried out using a tamp.

9. The method of claim 8, wherein said tamp has a cylindrical shape.

10. The method of claim 8, wherein said tamp has an outside shape approximating an implant to be implanted within the bone.

11. The method of claim 1, wherein said impacting step comprises using a plurality of tamps with sequentially increasing exterior sizes.

12. The method of claim 1, wherein said allograft bone particles comprise bone chips.

13. The method of claim 1, wherein said allograft bone particles have a controlled size and shape.

14. The method of claim 1, wherein said method steps are carried out on a proximal end of a femur.

15. The method of claim 1, comprising the further step of applying a bone growth enhancer to said form.

16. The method of claim 15, wherein said bone growth enhancer is coated onto said outside of said form.

17. The method of claim 15, wherein said bone growth enhancer is mixed with the allograft bone particles.

18. The method of claim 15, wherein said bone growth enhancer is selected from the group consisting of hydroxylapatite and HATCP.

19. An orthopaedic body for insertion into an opening in a bone during orthopaedic surgery, said orthopaedic body comprising:
   an impaction allograft form including a plurality of allograft bone particles frozen together with a predetermined outside shape, said form including a cannulation hole extending therethrough.

20. The orthopaedic body of claim 19, wherein said allograft form has an outside shape which is substantially cylindrical.

21. The orthopaedic body of claim 19, wherein said allograft form has an outside shape which approximates an implant to be implanted within the bone.

22. The orthopaedic body of claim 19, wherein said allograft form has an outside shape which approximates an intramedullary canal of the bone.

* * * * *